(12) United States Patent
Robinson et al.

(10) Patent No.: US 10,391,208 B2
(45) Date of Patent: *Aug. 27, 2019

(54) INSTILLATION CARTRIDGE AND THERAPY SYSTEM FOR NEGATIVE-PRESSURE THERAPY AND INSTILLATION THERAPY

(71) Applicant: KCI Licensing, Inc., San Antonio, TX (US)

(72) Inventors: Timothy Mark Robinson, Basingstoke (GB); Christopher Brian Locke, Bournemouth (GB); James A. Luckemeyer, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 688 days.

This patent is subject to a terminal disclaimer.

(21) Appl. No.: 14/794,340

(22) Filed: Jul. 8, 2015

(65) Prior Publication Data

US 2016/0015873 A1    Jan. 21, 2016

Related U.S. Application Data

(60) Provisional application No. 62/026,538, filed on Jul. 18, 2014.

(51) Int. Cl.
*A61M 1/00* (2006.01)
*A61M 5/142* (2006.01)
*A61M 3/02* (2006.01)

(52) U.S. Cl.
CPC ........ *A61M 1/0035* (2014.02); *A61M 1/0058* (2013.01); *A61M 1/0088* (2013.01);
(Continued)

(58) Field of Classification Search
CPC ... A61F 13/00017; A61B 42/00; A61B 46/00; A61B 17/32; A61B 17/3205;
(Continued)

(56) References Cited

U.S. PATENT DOCUMENTS 1,355,846 A    10/1920   Rannells
2,547,758 A    4/1951    Kelling
(Continued)

FOREIGN PATENT DOCUMENTS

AU    550575 B2    3/1986
AU    745271 B2    3/2002
(Continued)

OTHER PUBLICATIONS

International Search Report and Written Opinion corresponding to PCT Application No. PCT/US2015/039615 dated Oct. 1, 2015.
(Continued)

*Primary Examiner* — Tatyana Zalukaeva
*Assistant Examiner* — Gabriella E Burnette

(57) ABSTRACT

Systems, methods, and apparatuses for providing installation therapy and negative-pressure therapy are described. The apparatus includes a housing and a moveable barrier disposed in the housing to form a dosing chamber and a pressure chamber. The apparatus also includes a therapy conduit configured to be fluidly coupled to a pressure source and to a canister. The apparatus further includes a fluid inlet fluidly coupled to the dosing chamber and configured to be fluidly coupled to a fluid source and a fluid outlet fluidly coupled to the dosing chamber and configured to be fluidly coupled to a dressing. A pressure inlet is fluidly coupled to the therapy conduit and the pressure chamber; and a check valve is disposed in the therapy conduit.

59 Claims, 3 Drawing Sheets

(52) U.S. Cl.
CPC ...... *A61M 3/0254* (2013.01); *A61M 5/14224* (2013.01); *A61M 1/0084* (2013.01); *A61M 2205/123* (2013.01); *A61M 2205/128* (2013.01); *A61M 2205/3334* (2013.01); *A61M 2205/3337* (2013.01)

(58) Field of Classification Search
CPC .... A61M 1/0088; A61M 3/0254; A61M 5/14; A61M 1/0031
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,542,918 A * | 8/1996 | Atkinson ............ A61M 1/0064 417/401 |
| 5,549,584 A | 8/1996 | Gross |
| 5,554,011 A | 9/1996 | Bales et al. |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2012/0302976 A1* | 11/2012 | Locke ................ A61M 1/0084 604/318 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| WO | 99/13793 A1 | 3/1999 |
|---|---|---|
| WO | 2015066622 A1 | 5/2015 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

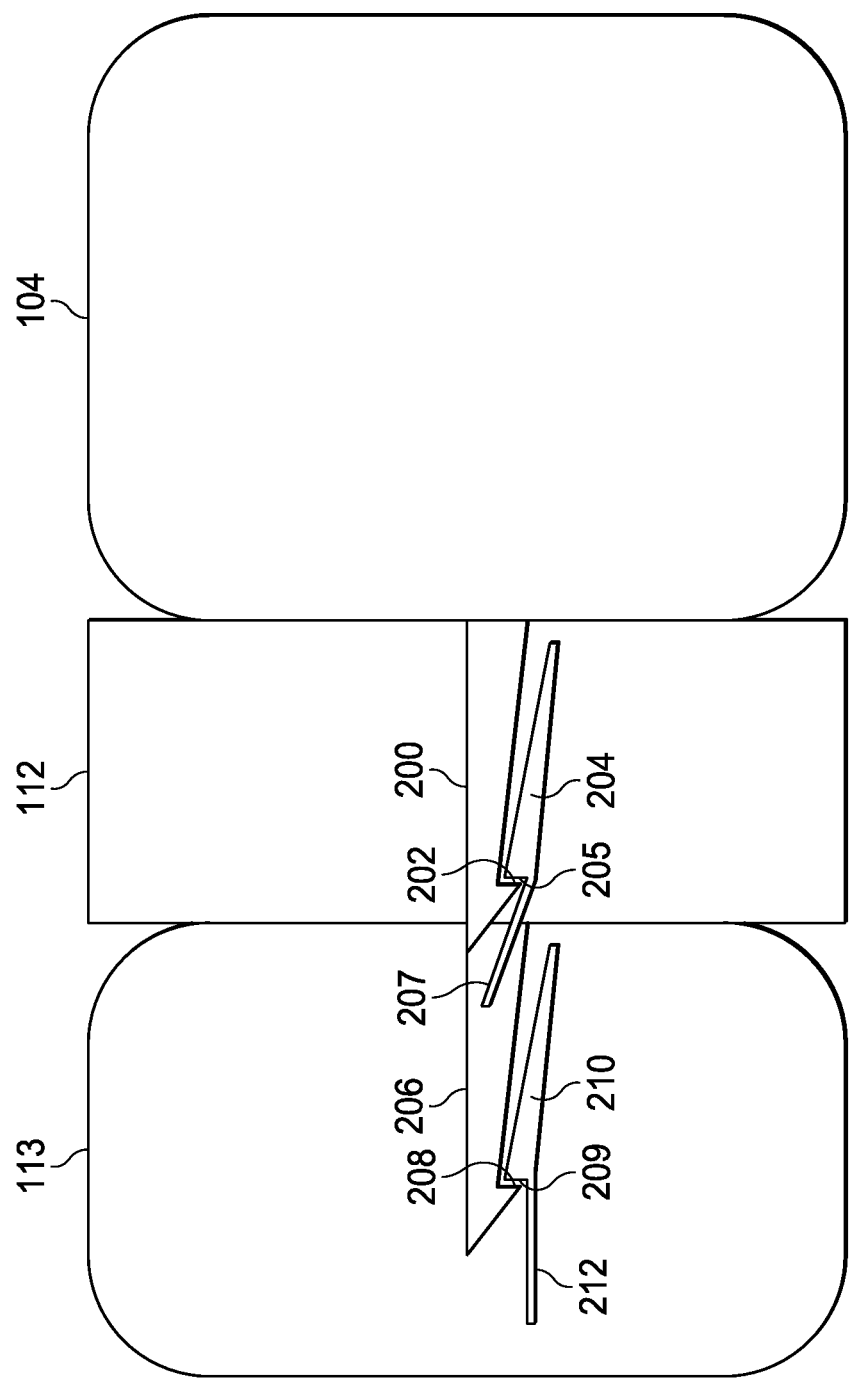

INSTILLATION CARTRIDGE AND THERAPY SYSTEM FOR NEGATIVE-PRESSURE THERAPY AND INSTILLATION THERAPY

The present invention claims the benefit, under 35 USC § 119(e), of the filing of U.S. Provisional Patent Application Ser. No. 62/026,538, entitled "Instillation Cartridge and Therapy System for Negative-Pressure Therapy and Instillation Therapy," by Robinson et al., filed Jul. 18, 2014, which is incorporated herein by reference for all purposes.

TECHNICAL FIELD

The invention set forth in the appended claims relates generally to tissue treatment systems and more particularly, but without limitation, to a disposable cartridge for use with a therapy system to provide negative-pressure therapy and instillation therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

In addition, the delivery of therapeutic fluids (e.g. saline or antibiotic fluids) to the tissue site can also provide benefits to healing of a tissue site. Treatment of tissue sites with the delivery of therapeutic fluids may also be referred to as "instillation therapy." Instillation therapy may assist in cleaning the tissue site by aiding in the removal of infectious agents or necrotic tissue. The therapeutic fluids used in instillation therapy may also provide medicinal fluids, such as antibiotics, anti-fungals, antiseptics, analgesics, or other similar substances, to aid in the treatment of a tissue site.

While the clinical benefits of negative-pressure therapy and instillation therapy are widely known, the cost and complexity of negative-pressure therapy and instillation therapy can be a limiting factor in its application, and the development and operation of delivery systems, components, and processes continues to present significant challenges to manufacturers, healthcare providers, and patients.

BRIEF SUMMARY

New and useful systems, apparatuses, and methods for instilling fluids in a negative-pressure therapy environment are set forth in the appended claims. Illustrative embodiments are also provided to enable a person skilled in the art to make and use the claimed subject matter. For example, an apparatus for providing installation therapy and negative-pressure therapy is described. The apparatus can include a housing and a moveable barrier disposed in the housing to form a dosing chamber and a pressure chamber. The apparatus can also include a therapy conduit configured to be fluidly coupled to a pressure source and to a canister. The apparatus can further include a fluid inlet fluidly coupled to the dosing chamber and configured to be fluidly coupled to a fluid source and a fluid outlet fluidly coupled to the dosing chamber and configured to be fluidly coupled to a dressing. A pressure inlet may be fluidly coupled to the therapy conduit and the pressure chamber, and a check valve is disposed in the therapy conduit.

In other embodiments, an apparatus for providing instillation therapy and negative-pressure therapy with a pressure source is described. The apparatus can include a therapy conduit configured to be fluidly coupled on a first end to the pressure source and on a second end to a canister, and a housing having a fluid inlet configured to be fluidly coupled to a fluid source, a fluid outlet configured to be fluidly coupled to a dressing, and a pressure inlet fluidly coupled to the therapy conduit. A moveable barrier may be disposed in the housing to form a dosing chamber and a pressure chamber. The dosing chamber and the pressure chamber may be fluidly isolated from each other. The fluid inlet and the fluid outlet may be in fluid communication with the dosing chamber, and the pressure inlet may be in fluid communication with the pressure chamber. The apparatus may also include a check valve fluidly coupled to the therapy conduit and the pressure inlet.

In still other embodiments, a therapy system for providing instillation therapy and negative-pressure therapy is described. The system may include a pump having a pump inlet and a pump outlet. The pump may be configured to draw fluid into the pump inlet and move fluid out of the pump outlet. The system may also include a fluid source and an adapter coupled to the pump and the fluid source. The adapter may include a therapy conduit configured to be fluidly coupled on a first end to the pump and on a second end to a canister. The adapter may also include a housing having a fluid inlet configured to be fluidly coupled to the fluid source, a fluid outlet configured to be fluidly coupled to a dressing, and a pressure inlet fluidly coupled to the therapy conduit. A moveable barrier may be disposed in the housing to form a dosing chamber and a pressure chamber. The dosing chamber and the pressure chamber may be fluidly isolated from each other. The fluid inlet and the fluid outlet may be in fluid communication with the dosing chamber, and the pressure inlet may be in fluid communication with the pressure chamber. The adapter may also include a check valve fluidly coupled to the therapy conduit and the pressure inlet. The system may further include a selector valve fluidly coupled to the pump inlet and the pump outlet. The selector valve may be configured to be fluidly coupled to the therapy conduit. The selector valve may have a first position fluidly coupling the pump inlet to the therapy conduit and a second position fluidly coupling the pump outlet to the therapy conduit.

In yet other embodiments, a method for providing instillation therapy and negative-pressure therapy is described. A pressure source having a selector valve, a canister, a fluid source, a dressing, and an adapter may be provided. The adapter may include a therapy conduit and a housing having a fluid inlet, a fluid outlet, and a pressure inlet fluidly coupled to the therapy conduit. The adapter may also include a moveable barrier disposed in the housing to form a dosing chamber and a pressure chamber. The dosing chamber and the pressure chamber may be fluidly isolated from each other. The fluid inlet and the fluid outlet may be in fluid communication with the dosing chamber, and the pressure inlet may be in fluid communication with the pressure chamber. A check valve may be fluidly coupled to the therapy conduit and the pressure inlet. The therapy conduit may be fluidly coupled to the pressure source and the canister, the fluid source may be fluidly coupled to the fluid inlet, and the fluid outlet may be fluidly coupled to the dressing. The selector valve may be operated to select a therapy mode, and the pressure source may be operated in response to the therapy mode selection.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 5 is a schematic diagram illustrating additional details that may be associated with an attachment system of the therapy system of FIG. 1.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
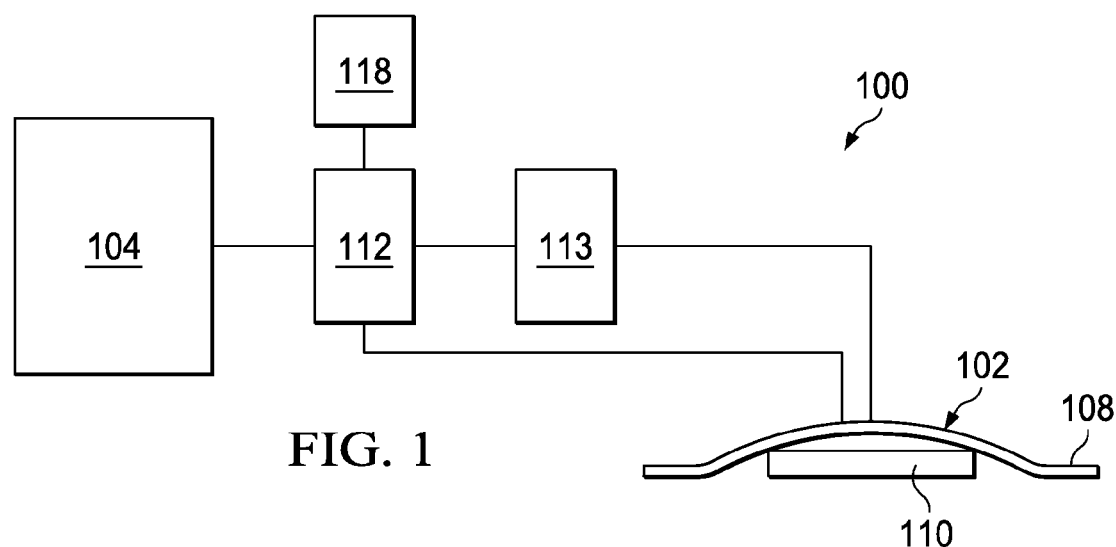
FIG. 1 is a functional block diagram of an example embodiment of a therapy system that can provide instillation fluid in accordance with this specification.

FIG. 1 is a simplified functional block diagram of an example embodiment of a therapy system 100 that can provide instillation therapy and negative-pressure therapy in accordance with this specification. The therapy system 100 may include a dressing and a pressure source. For example, a dressing 102 may be fluidly coupled to a pressure source 104, as illustrated in FIG. 1. A dressing generally includes a cover and a tissue interface. The dressing 102, for example, includes a cover 108, and a tissue interface 110. The therapy system 100 may also include a container, such as a canister 113, fluidly coupled to the dressing 102 and to the pressure source 104. In some embodiments, the therapy system 100 may further include an adapter for fluid instillation, such as a cartridge 112, fluidly coupled to the dressing 102 and the pressure source 104. In some embodiments, the cartridge 112 may be fluidly coupled between the pressure source 104 and the canister 113. In some embodiments, the cartridge 112 may be directly fluidly coupled to both the canister 113 and the dressing 102. In some embodiments, a fluid source, such as a fluid source 118, may be fluidly coupled to the cartridge 112.

In general, components of the therapy system 100 may be coupled directly or indirectly. For example, the pressure source 104 may be directly coupled to the canister 113 and indirectly coupled to the dressing 102 through the canister 113. Components may be fluidly coupled to each other to provide a path for transferring fluids (i.e., liquid and/or gas) between the components.

In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected and disposed of properly.

The fluid mechanics of using a pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically refers to a position in a fluid path relatively closer to a pressure source, and conversely, the term "upstream" refers to a position relatively further away from a pressure source. Similarly, it may be convenient to describe certain features in terms of fluid "inlet" or "outlet" in such a frame of reference. This orientation is generally presumed for purposes of describing various features and components of therapy systems herein. However, the fluid path may also be reversed in some applications (such as by substituting a positive-pressure source for a pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. "Positive pressure" generally refers to a pressure greater than a local ambient pressure. References to increases in positive pressure typically refer to an increase in absolute pressure, while decreases in positive pressure typically refer to a decrease in absolute pressure.

A pressure source, such as the pressure source 104, may be a reservoir of air at a negative pressure, or may be a manual or electrically-powered device that can reduce the pressure in a sealed volume, such as a pump, a charge pump, a wall charge port available at many healthcare facilities, or a micro-pump, for example. A pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A pressure source may also be a reservoir of air at a positive pressure, or may be a manual or electrically-powered device that can increase the pressure in a sealed volume, such as a pump, a suction pump, a wall suction port available at many healthcare facilities, or a micro-pump, for example. A pressure source may be housed within or used in conjunction with other components, such as sensors, processing units, alarm indicators, memory, databases, software, display devices, or user interfaces that further facilitate therapy. While the amount and nature of positive pressure applied by a pressure source may vary, the pressure is generally between 5 mm Hg (667 Pa) and 500 mm Hg (66.7 kPa) and commonly applied at about 100 mm Hg.

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLAIPGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 grams per square meter (gsm). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The canister 113 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. The canister 113 is also representative of a fluid management device that is operable to regulate the delivery of instillation fluid.

The dressing 102 may also be used to provide a sealed therapeutic environment for instillation therapy. Instillation therapy may include the slow introduction of a solution to a tissue site. The solution may be used to provide moisture to the tissue site, to provide warmth or cold to the tissue site, to provide a drug to the tissue site, to soak a tissue site, or to provide another substance to the tissue site. Often, different types of instillation therapy may require a different type of instillation fluid to achieve a desired effect. For example, a first type of fluid may provide moisture to the tissue site. A different type of fluid may supply a drug to the tissue site. Many times, the need for different types of fluid to treat the tissue site may make instillation therapy time consuming to administer.

Some patients may experience improved outcomes with a combined treatment that includes using both negative-pressure therapy and instillation therapy. Existing therapy systems that provide instillation or irrigation of a tissue site as well as negative-pressure therapy can be complicated to use and setup. Multiple tubes, clamps, and interfaces may often be needed to properly apply both negative pressure and fluid to the tissue site. For example, to set up a therapy system having both negative-pressure therapy and instillation therapy, components for both systems may be placed proximate to a patient. Unfortunately, the cost of a combined treatment system can be prohibitive in many clinical environments, reducing the likelihood that a patient may receive the benefits of a combined system.

In many clinical environments, a dedicated negative-pressure therapy system provides negative-pressure therapy to a tissue site. The dedicated negative-pressure therapy system may be positioned proximate to a patient receiving negative-pressure therapy and the dedicated negative-pressure therapy system may be fluidly coupled to a tissue site to provide negative-pressure therapy. Similarly, instillation therapy often relies on a dedicated instillation therapy system to provide instillation therapy to a tissue site. The dedicated instillation therapy system may also be positioned proximate to a patient receiving instillation therapy, and the dedicated instillation therapy device may be fluidly coupled to a tissue site to provide instillation therapy. Having both negative-pressure therapy system components and instillation therapy system components proximate to a patient may make the area around the patient cluttered, which can lead to negative outcomes for the patient.

Both dedicated negative-pressure therapy systems and dedicated instillation therapy systems may be expensive. Generally, given the costs associated with negative-pressure therapy and instillation therapy, medical facilities may not be willing to purchase both a dedicated negative-pressure therapy system and a dedicated instillation therapy system. As a result, some clinical facilities may choose to forgo some types of clinical treatment. For example, some clinical facilities may maintain a dedicated negative-pressure therapy system to provide negative-pressure therapy. If a patient requires instillation therapy, a clinician may be required to physically administer instillation therapy, such as with a syringe. Application of instillation therapy in this manner may also require the clinician to remove the dressing, which can cause pain to the patient and potentially increase infection risks. Physical administration of instillation therapy can require a significant investment of clinician time, increase the likelihood of misapplication of therapy, and potentially increase the risk of infection of a tissue site.

Some clinical facilities employ multi-channel dedicated negative-pressure therapy systems. A multi-channel negative-pressure therapy system may be capable of providing negative-pressure therapy to more than one tissue site at a time. A multi-channel negative-pressure therapy system may be large and inhibit placement of other devices near a patient. If instillation therapy is also needed, it may be difficult to place a dedicated instillation therapy system proximate to a patient. Consequently, a clinician may be required to physically administer instillation therapy, which can cause some or all of the complications previously described.

The therapy system 100 described herein can solve these problems and others by managing pressure to deliver negative-pressure therapy and instillation fluids. In some embodiments, the therapy system 100 can provide negative-pressure therapy to the tissue site. For example, the cartridge 112 can be fluidly coupled to the dressing 102 and the pressure source 104, which can be operated to provide negative pressure to provide negative-pressure therapy. Additionally, the therapy system 100 can also provide instillation therapy in some embodiments. For example, the cartridge 112 can be fluidly coupled to the dressing 102 and the pressure source 104, which can be operated to provide positive pressure for instillation therapy. In some embodiments, the therapy system 100 can provide alternating negative-pressure therapy and instillation therapy. For example, the pressure source 104 may be fluidly coupled to the cartridge 112 and the canister 113 and operated to provide both negative-pressure therapy and instillation therapy.

Figure 2:
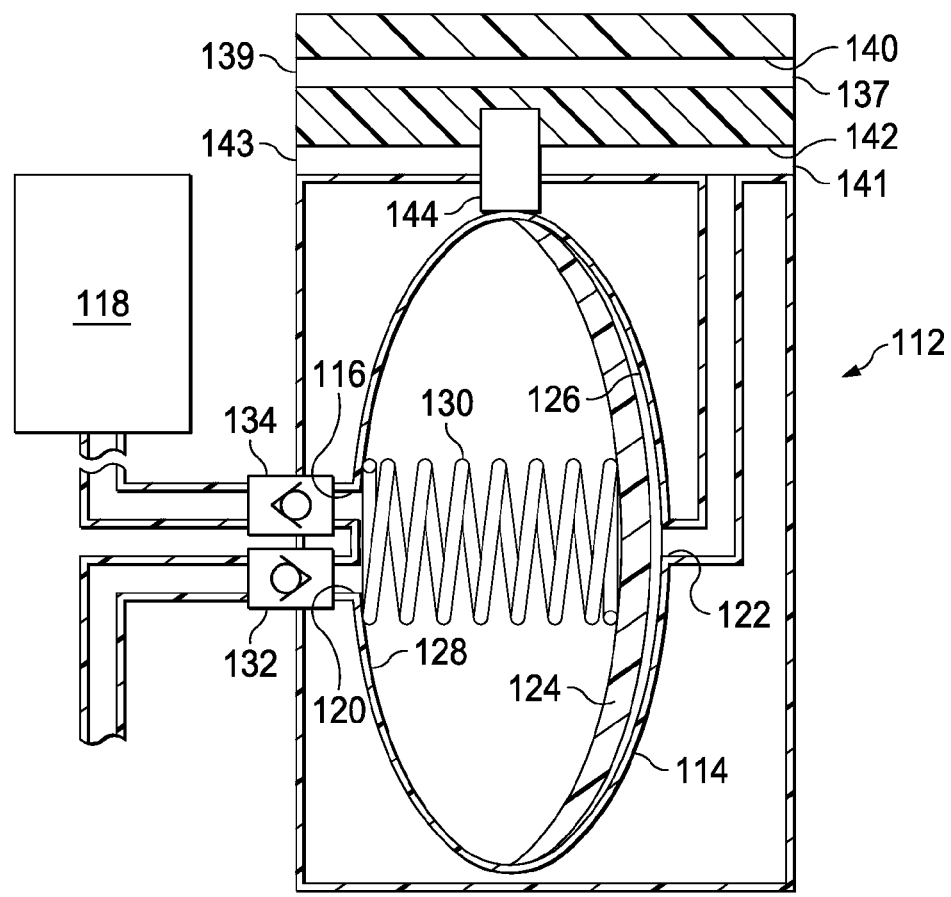
FIG. 2 is a schematic sectional diagram illustrating additional details that may be associated with an example embodiment of a cartridge of the therapy system of FIG. 1.

FIG. 2 is a schematic sectional diagram, illustrating additional details that may be associated with some example embodiments of the cartridge 112 in a first state. Generally, the cartridge 112 may have many different shapes and sizes. In some embodiments, the cartridge 112 may be manufactured to physically couple to existing negative-pressure therapy products. In some embodiments, the cartridge 112 may be disposable, single-patient use, and replaceable every two to three days. In some embodiments, the cartridge 112 may be about 2 inches thick or less. In some embodiments, the cartridge may be formed of injection molded plastic, such as polycarbonate plastic, acrylonitrile butadiene styrene, or a blend of the two. In some embodiments, the cartridge 112 may have internal components formed of silicone and thermoplastic elastomer materials and may be sterilized during assembly.

The cartridge 112 may have a housing 114. In some embodiments, the housing 114 may be disposed inside another container so that the housing 114 may be enclosed in the cartridge 112. In other embodiments, the housing 114 may form an outer portion of the cartridge 112. In some embodiments, the housing 114 may generally define a chamber and have a structural arrangement to fluidly isolate the chamber from the ambient environment. In some embodiments, the housing 114 may be an ellipsoid and form an ellipsoid chamber having an elliptical cross-section. In other embodiments, the housing 114 may have other suitable shapes, such as spherical, cuboid, or amorphous shaped forming similarly shaped chambers having similarly shaped cross-sections. In some embodiments, the shape of the chamber may not correspond with the shape of the housing 114. In some embodiments, the housing 114 may be formed of plastic, such as EASTAR™ DN004 produced by Eastman Chemical Company. In other embodiments, the housing 114 may be formed of Terlux® 2802HD or Terlux® 2822HD produced by Styrolution Group GmbH.

In some embodiments, a barrier may be disposed within the chamber of the housing 114. A barrier may be a solid object positioned within the chamber of the housing 114 to divide the chamber of the housing 114 into two separate fluid chambers. In some embodiments, a portion or an entirety of a barrier may be moveable, such as a piston or a diaphragm 124, to adjust respective volumes of the fluid chambers created by the barrier. In some embodiments, the diaphragm 124 may be a membrane or a sheet of semi-flexible material having a periphery. The periphery of the diaphragm 124 may be coupled to the housing 114 to form a pressure chamber 126 and a dosing chamber 128. Generally, the periphery of the diaphragm 124 may be coupled to the housing 114 so that the pressure chamber 126 is fluidly isolated from the dosing chamber 128. For example, the diaphragm 124 may be sealed to the housing 114, may be welded to the housing 114, or may be otherwise coupled to the housing 114 to prevent fluid movement across the diaphragm 124. In some embodiments, the diaphragm 124 may be formed of an elastic or a semi-elastic material. In some embodiments, the diaphragm 124 may be formed of rubber, thermoplastic, or polytetrafluoroethlyene.

In some embodiments, the periphery of the diaphragm 124 may be coupled to the housing 114 so that the diaphragm 124 may flex between a discharge position and a charge position. The discharge position of the diaphragm 124 may be the position of the diaphragm 124 that maximizes the volume of the pressure chamber 126 and minimizes the volume of the dosing chamber 128. The charge position of the diaphragm 124 may be the position of the diaphragm 124 that maximizes the volume of the dosing chamber 128 and minimizes the volume of the pressure chamber 126. In some embodiments, the periphery of the diaphragm 124 may be coupled proximate to a center of a cross-section of the housing 114. For example, the housing 114 may form an ovoid or elliptical-shaped chamber having a transverse diameter and a conjugate diameter. In some embodiments, the periphery of the diaphragm 124 may be coupled to the housing 114 so that the diaphragm 124 coincides with the transverse diameter if the volumes of the pressure chamber 126 and the dosing chamber 128 are equal, as shown in FIG. 2. In other embodiments, the diaphragm 124 may be coupled to the housing 114 in other locations of the housing 114.

In some embodiments, the dimensions of the diaphragm 124, the pressure chamber 126, and the dosing chamber 128 may be determined by the amount of fluid needed to provide instillation. For example, a tissue site may need approximately 5 milliliters of fluid to be dispensed with each operation of the cartridge 112. Consequently, the dosing chamber 128 may have a volume of about 5 milliliters if the diaphragm 124 is in the charge position, and the pressure chamber 126 may have a volume of about 5 milliliters if the diaphragm 124 is in the discharge position. If the housing 114 is spherical, then the dosing chamber 128 may have a volume given by:

$$4/3\pi \times r^3 = V$$

where r is the radius of a spherical housing 114 in millimeters and V is the volume of the spherical housing 114 in milliliters. For an exemplary 5 milliliter volume, the radius of the dosing chamber 128 if the diaphragm 124 is in the charge position is about 10.6 millimeters. In some embodiments, the diaphragm 124 may have a radius approximately equal to the radius of the dosing chamber 128 if the diaphragm 124 is in the charge position. Similarly, the pressure chamber 126 may have a radius of about 10.6 millimeters if the diaphragm 124 is in the discharge position. In some embodiments, the volume of the dosing chamber 128 if the diaphragm 124 is in the charge position is between about 5 milliliters and about 10 milliliters. In other embodiments, the volume of the dosing chamber 128 may be varied as needed to administer a therapeutic amount of fluid to a tissue site.

In some embodiments, the housing 114 may be formed of two sheets of a polymer film having peripheral portions. The peripheral portions of each sheet may be coupled together, such as by welding, adhering, or otherwise securing the peripheral portions of each sheet to each other. In some embodiments, a third sheet of polymer material may be disposed between the first sheet and the second sheet of polymer material. The third sheet may have peripheral portions coupled to the peripheral portions of the first and second sheet of polymer material to form the diaphragm 124, the pressure chamber 126, and the dosing chamber 128.

In some embodiments, the housing 114 may have a pressure inlet 122. The pressure inlet 122 may be a fluid passage formed in the housing 114 to provide fluid communication with the pressure chamber 126. In some embodiments, the pressure inlet 122 may be a tube having at least one lumen. The tube may be coupled to the housing 114 so that the lumen of the tube is in fluid communication with the pressure chamber 126. In some embodiments, the pressure inlet 122 may be further fluidly coupled to the pressure source 104.

In some embodiments, the diaphragm 124 may be biased to the charge position. For example, a biasing element may be disposed in the pressure chamber 126 to bias the diaphragm 124 to the discharge position. A biasing element may be a spring 130, for example. The spring 130 may have a first end coupled to the housing 114 and a second end coupled to the diaphragm 124. The spring 130 may have an unloaded position and a loaded position. Generally, if no external force is acting on the spring 130, the spring 130 is in the unloaded position. If the spring 130 is compressed or extended, the spring 130 may be in the loaded position. Generally, a spring may exert a reactive force in response to displacement from the unloaded position. The reactive force is generally proportional to the distance a spring is either compressed or extended if an external force loads the spring. As shown in FIG. 2, the spring 130 may be unloaded.

In some embodiments, the biasing element may be a foam disposed in the pressure chamber 126. In some embodiments, the foam may be an open-cell reticulated foam having a spring rate similar to the spring 130. In some embodiments, for example, if the housing 114 comprises a cylindrical construction, the foam may be configured to compress along a length of the cylinder in response to the application of negative pressure.

In some embodiments, the housing 114 may include a fluid inlet 116. The fluid inlet 116 may be a fluid passage coupled to the housing 114. In some embodiments, the fluid inlet 116 may be a tube having at least one lumen. The tube may be coupled to the housing 114 so that the at least one lumen of the tube is in fluid communication with the dosing chamber 128. In some embodiments, the fluid inlet 116 may be further fluidly coupled to a fluid source 118. The fluid source 118 may be a reservoir of fluid, such as instillation fluid, for example. In some embodiments, the fluid source 118 may be a reservoir of fluid suspended from an intravenous pole proximate to the pressure source 104 or the cartridge 112. In some embodiments, the fluid source 118 may an intravenous bag having instillation fluid stored therein.

In some embodiments, a valve 134 may be fluidly coupled to the fluid inlet 116. In some embodiments, the valve 134 may be coupled to the housing 114 and the fluid inlet 116 may be coupled to the valve 134 so that the valve 134 is fluidly coupled between the fluid inlet 116 and the fluid source 118. In other embodiments, the valve 134 may be coupled in other locations. In some embodiments, the valve 134 is a check valve. A check valve may be a valve that permits one-way flow of fluid through the valve. In some embodiments, the valve 134 may be a spring-loaded check valve having a cracking pressure that is responsive to a low vacuum. For example, the valve 134 may open in response to a pressure differential of less than about 125 mm Hg negative pressure. In some embodiments, the valve 134 may be fluidly coupled to the fluid inlet 116 to permit fluid flow into the dosing chamber 128 and prevent fluid flow from the dosing chamber 128.

In some embodiments, the cartridge 112 may also have a fluid outlet 120. The fluid outlet 120 may be a fluid passage coupled to the housing 114 to provide fluid communication with the dosing chamber 128. In some embodiments, the fluid outlet 120 may be a tube having at least one lumen. The tube may be coupled to the housing 114 so that a lumen is in fluid communication with the dosing chamber 128. In some embodiments, the fluid outlet 120 may be further fluidly coupled to a dressing, such as the dressing 102. If the fluid outlet 120 is fluidly coupled to the dressing 102, the dressing 102 may be in fluid communication with the dosing chamber 128 through the fluid outlet 120.

In some embodiments, a valve 132 may be fluidly coupled to the fluid outlet 120. In some embodiments, the valve 132 may be coupled to the fluid outlet 120 so that the valve 132 allows fluid flow through the fluid outlet 120. In other embodiments, the valve 132 may be coupled in other locations. In some embodiments, the valve 132 is a check valve. A check valve may be a valve that permits one-way flow of fluid through the valve. In some embodiments, the valve 132 may be a spring-loaded check valve having a cracking pressure that is responsive to low positive pressures. For example, the valve 132 may open in response to a pressure differential of less than about 125 mm Hg positive pressure. In some embodiments, the valve 132 may be fluidly coupled to the fluid outlet 120 to prevent fluid flow into the dosing chamber 128 through the fluid outlet 120 and permit fluid flow from the dosing chamber 128. In some embodiments, the valve 132 may be a vacuum occluder configured to prevent or limit fluid flow through the fluid outlet 120 if there is a negative pressure in the dosing chamber 128.

In some embodiments, the cartridge 112 may include a pressure-sensing conduit 140. The pressure-sensing conduit 140 may be a tube or other fluid passage extending through the cartridge 112. In some embodiments, the pressure-sensing conduit 140 may have a first end 137 configured to be fluidly coupled to the pressure source 104 and a second end 139 configured to be fluidly coupled to the canister 113. Generally, the pressure-sensing conduit 140 may allow fluid communication through the cartridge 112. In some embodiments, a pressure sensor may be fluidly coupled to the first end 137 of the pressure-sensing conduit 140. If the canister 113 is fluidly coupled to the second end 139 of the pressure-sensing conduit 140, the pressure in the canister 113 may be fluidly communicated through the pressure-sensing conduit 140 to the pressure sensor of the pressure source 104. In some embodiments, the pressure-sensing conduit 140 may include one or more hydrophobic filters or odor control activated carbon filters.

In some embodiments, the cartridge 112 may also include a therapy conduit 142. The therapy conduit 142 may be a tube or other fluid passage extending through the cartridge 112. In some embodiments, the therapy conduit 142 may have a first end 141 configured to be fluidly coupled to the pressure source 104 and a second end 143 configured to be fluidly coupled to the canister 113. Generally, the therapy conduit 142 may allow fluid communication through the cartridge 112. In some embodiments, the pressure source 104 may be fluidly coupled to the first end 141 of the therapy conduit 142. If the canister 113 is fluidly coupled to the second end 143 of the therapy conduit 142, the pressure source 104 may be operated to move fluid through the therapy conduit 142. In some embodiments, the pressure inlet 122 may be fluidly coupled to the therapy conduit 142. In some embodiments, the therapy conduit 142 may include one or more hydrophobic filters or odor control activated carbon filters.

In some embodiments, a valve 144 may be fluidly coupled to the therapy conduit 142. The valve 144 may be fluidly coupled between the pressure inlet 122 and the second end 143 of the therapy conduit 142. In some embodiments, the valve 144 may be a check valve configured to permit fluid flow from the second end 143 of the therapy conduit 142 to the first end 141 of the therapy conduit 142 and prevent fluid flow from the first end 141 of the therapy conduit 142 to the second end 143 of the therapy conduit 142. In some embodiments, the valve 144 may be a reed type valve. A reed valve may be a check valve having a flap covering an opening. Flow through the reed valve in a first direction may move the flap away from the opening, and flow through the reed valve in a second direction that is opposite the first direction may move the flap into tighter contact with the opening, preventing fluid flow. A reed valve may provide almost no pressure drop and may be inexpensive to manufacture.

Figure 3:
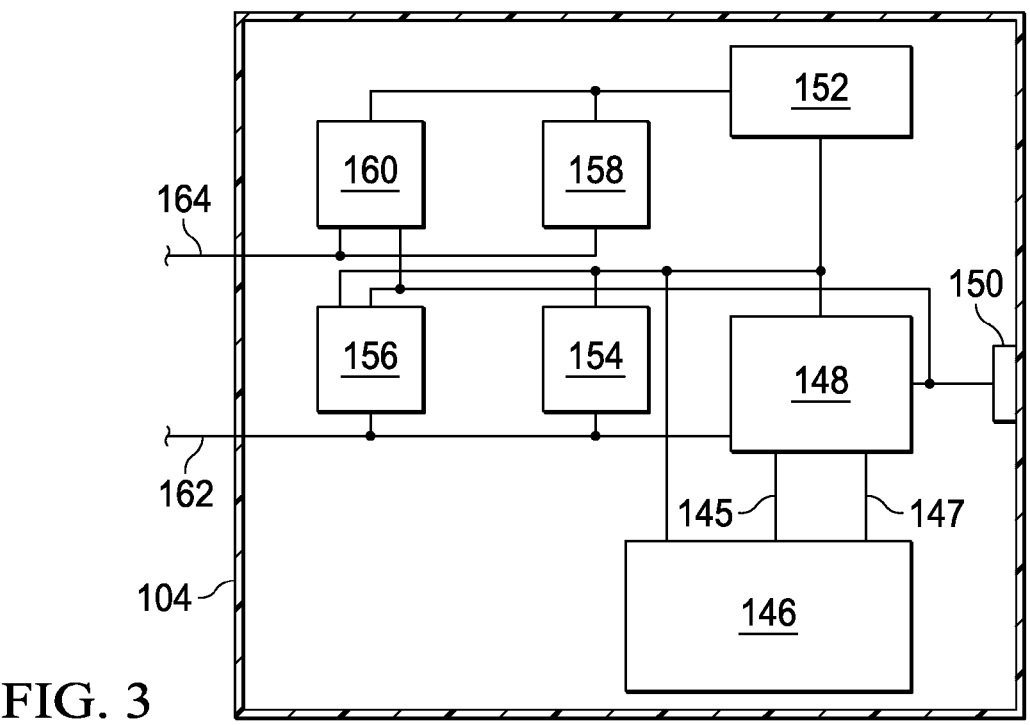
FIG. 3 is a schematic sectional diagram illustrating additional details that may be associated with a pressure source of the therapy system of FIG. 1.

FIG. 3 is a schematic view, illustrating additional details that may be associated with some embodiments of the pressure source 104. In some embodiments, the pressure source 104 may include a pump 146. The pump 146 may be fluidly coupled to a selector valve 148 and communicatively coupled to a controller 152. The selector valve 148 may be further fluidly coupled to a vent 150 and a pump pressure sensor 154. The selector valve 148 and the pump pressure sensor 154 may also be communicatively coupled to the controller 152. In some embodiments, the pressure source 104 may also include a vent valve 156 that is fluidly coupled to the pump pressure sensor 154 and a therapy port 162. The vent valve 156 may also be communicatively coupled to the controller 152. In some embodiments, the pressure source 104 may further include a therapy-pressure sensor 158 fluidly coupled to a pressure-relief valve 160 and a pressure-sensing port 164. The therapy-pressure sensor 158 and the pressure-relief valve 160 may be further fluidly coupled to the controller 152. The vent valve 156 and the pressure-relief valve 160 may each be further fluidly coupled to the ambient environment, such as to the vent 150.

In some embodiments, the pump 146 may have a pump inlet 145 and a pump outlet 147. The pump inlet 145 may be a fluid connection through which the pump 146 draws fluid into the pump 146. The pump outlet 147 may be a fluid connection through which the pump forces fluid out of the pump 146. In some embodiments, both the pump inlet 145 and the pump outlet 147 may be fluidly coupled to the selector valve 148. In some embodiments, the pump 146 may be a diaphragm pump driven by an electric motor. A diaphragm pump may be a positive displacement pump formed from a chamber having a reciprocating diaphragm. The chamber may have an inlet and an outlet, each having a valve operable to permit flow in one direction. The reciprocating diaphragm may form a portion of the chamber. The reciprocating action of the diaphragm can cause the volume of the chamber to change, drawing fluid into the chamber when the volume is increased and forcing fluid out of the chamber when the volume is decreased. In other embodiments, the pump 146 may be other pump types operable to generate negative pressures as described herein. For example, the pump 146 may be a reversible pump capable of drawing fluid through both the pump inlet 145 and the pump outlet 147.

In some embodiments, the pump 146 may have a free-air-flow capacity between about 7 liters per minute (lpm) to about 9 lpm. Free-air-flow capacity may refer to the volume of air that may be moved by a pump when the pump is operated in a free space. In some embodiments, the pump 146 may be configured to operate at about 2 lpm. In some embodiments, a Parker Hannifin Corporation BTC-IIS Diaphragm Pump may be used. In some embodiments, a Thomas Products Division, Manufacturer Part No. 14210001 type diaphragm pump may be used.

A pressure sensor, such as the pump pressure sensor 154 or the therapy-pressure sensor 158, may be a piezoresistive strain gauge, a capacitive sensor, an electromagnetic sensor, a piezoelectric sensor, an optical sensor, or a potentiometric sensor, for example. In some embodiments, a pressure sensor can measure a strain caused by an applied pressure. A pressure sensor may be calibrated by relating a known amount of strain to a known pressure applied. The known relationship may be used to determine an unknown applied pressure based on a measured amount of strain. In some embodiments, a pressure sensor may include a receptacle configured to receive an applied pressure.

Generally, a "valve," such as the vent valve 156, the pressure-relief valve 160, or the selector valve 148, may be a device configured to selectively permit fluid flow through the device. A valve may be a ball valve, a gate valve, a butterfly valve, or other valve type that may be operated to control fluid flow through the valve. Generally, a valve may include a valve body having a flow passage, a valve member disposed in the flow passage and operable to selectively block the flow passage, and an actuator configured to operate the valve member. The flow passage may have an inlet and an outlet. An actuator may be configured to position the valve member in a closed position, preventing fluid flow through the flow passage of the valve; an open position, permitting fluid flow through the fluid passage of the valve; or a metering position, permitting fluid flow through the flow passage of the valve at a selected flow rate. In some embodiments, the actuator may be a mechanical actuator configured to be operated by an operator. In some embodiments, the actuator may be an electromechanical actuator configured to be operated in response to the receipt of a signal input, such as a solenoid valve. For example, the actuator may include an electrical motor configured to receive a signal from a controller. In response to the signal, the electrical motor of the actuator may move the valve member of the valve. In some embodiments, the actuator may be a pneumatically operated actuator configured to be operated in response to receipt of a pneumatic input. In some embodiments, a pneumatic input may be negative pressure or positive pressure provided by a pump.

A flow capacity for a valve may be selected to minimize pressure drop across the valve while providing a desired flow rate. In some embodiments, a valve may be selected to provide about 2 lpm flow through the valve. In some embodiments, a valve may be a pinch valve. A pinch valve may be a portion of a tube having a clamping device positioned to selectively compress the tube to block passage of fluid through the tube. In some embodiments, the portion of a tube may be a tube formed of an elastomer. In some embodiments, the portion of a tube may be a tube formed of a silicone.

In some embodiments, the selector valve 148 may be a four-way valve having four ports so that up to four devices may be directly fluidly coupled to the selector valve 148. For example, the selector valve 148 may be fluidly coupled to both the pump inlet 145 and the pump outlet 147 of the pump 146, as well as the pump pressure sensor 154 and the vent 150. Generally, a four-way valve may have four ports and two fluidly isolated passages extending through the four-way valve. Each passage may fluidly couple to separate ports to provide two flow paths through the four-way valve. The passages may then be moved to fluidly couple two different ports to provide two different flow paths through the four-way valve. In some embodiments, the selector valve 148 may be operable to fluidly couple the pump inlet 145 to the therapy port 162 and the pump outlet 147 to the vent 150 in a first position. The selector valve 148 may be operated to fluidly couple the pump inlet 145 to the vent 150 and the pump outlet 147 to the therapy port 162 in a second position. In some embodiments, the selector valve 148 may be a solenoid operated four-way valve produced by MAC © Valves. In other embodiments, the selector valve 148 may be a manually operated valve. In some embodiments, the selector valve 148 may accommodate about 2 lpm flow with a minimal pressure drop.

The controller 152 may be communicatively coupled to the pump 146, the selector valve 148, the pump pressure sensor 154, the vent valve 156, the therapy-pressure sensor 158, and the pressure-relief valve 160. The controller 152 may be operable to actuate the pump 146, the selector valve 148, the pump pressure sensor 154, the vent valve 156, the therapy-pressure sensor 158, and the pressure-relief valve 160 to provide negative-pressure therapy and instillation therapy.

As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, communicative coupling between a controller and other devices may be one-way communication. In one-way communication, signals may only be sent in one direction. For example, a sensor may generate a signal that may be communicated to a controller, but the controller may not be capable of sending a signal to the sensor. In some embodiments, communicative coupling between a controller and another device may be two-way communication. In two-way communication, signals may be sent in both directions. For example, a controller and a user interface may be communicatively coupled so that the controller may send and receive signals from the user interface. Similarly, a user interface may send and receive signals from a controller. In some embodiments, signal transmission between a controller and another device may be referred to as the controller operating the device. For example, interaction between a controller and a valve may be referred to as the controller operating the valve; placing the valve in an open position, a closed position, or a metering position; and opening the valve, closing the valve, or metering the valve.

A controller, such as the controller 152, may be a computing device or system, such as a programmable logic controller, or a data processing system, for example. In some embodiments, a controller may be configured to receive input from one or more devices, such as a user interface, a sensor, or a flow meter, for example. In some embodiments, a controller may receive input, such as an electrical signal, from an alternative source, such as through an electrical port, for example.

In some embodiments, a controller may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, a controller may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

The pressure source 104 may include a user interface. A user interface may be a device configured to allow communication between a controller, such as the controller 152, and an environment external to a pressure source 104. In some embodiments, an external environment may include an operator or a computer system configured to interface with a pressure source 104, for example. In some embodiments, a user interface may receive a signal from a controller and present the signal in a manner that may be understood by an external environment. In some embodiments, a user interface may receive signals from an external environment and, in response, send signals to a controller.

In some embodiments, a user interface may be a graphical user interface, a touchscreen, or one or more motion tracking devices. A user interface may also include one or more display screens, such as a liquid crystal display ("LCD"), lighting devices, such as light emitting diodes ("LED") of various colors, and audible indicators, such as a whistle, configured to emit a sound that may be heard by an operator. A user interface may further include one or more devices, such as knobs, buttons, keyboards, remotes, touchscreens, ports that may be configured to receive a discrete or continuous signal from another device, or other similar devices; these devices may be configured to permit the external environment to interact with the user interface. A user interface may permit an external environment to select a therapy to be performed with a pressure source 104. In some embodiments, a user interface may display information for an external environment such as a duration of therapy, a type of therapy, an amount of negative pressure being supplied, an amount of instillation solution being provided, a fluid level of a container, or a fluid level of a cartridge, for example.

A pressure source 104 may also include a power source. A power source may be a device that supplies electric power to an electric load. A power source may include a battery, a direct current (DC) power supply, an alternating current (AC) power supply, a linear regulated power supply, or a switched-mode power supply, for example. A power supply may supply electric power to a controller, a sensor, a flow meter, a valve, a user interface, or a pump, for example.

The vent 150 may be an opening disposed on an exterior of the pressure source 104. The vent 150 may be a device configured to fluidly couple the exterior to an interior of the pressure source 104. The therapy port 162 may be a port disposed on an exterior of the pressure source 104. The therapy port 162 may be a device configured to provide a fluid path to an interior of the pressure source 104. The pressure-sensing port 164 may be a port disposed on an exterior of the pressure source 104. The pressure-sensing port 164 may be a device configured to provide a fluid path to an interior of the pressure source 104.

Figure 4:
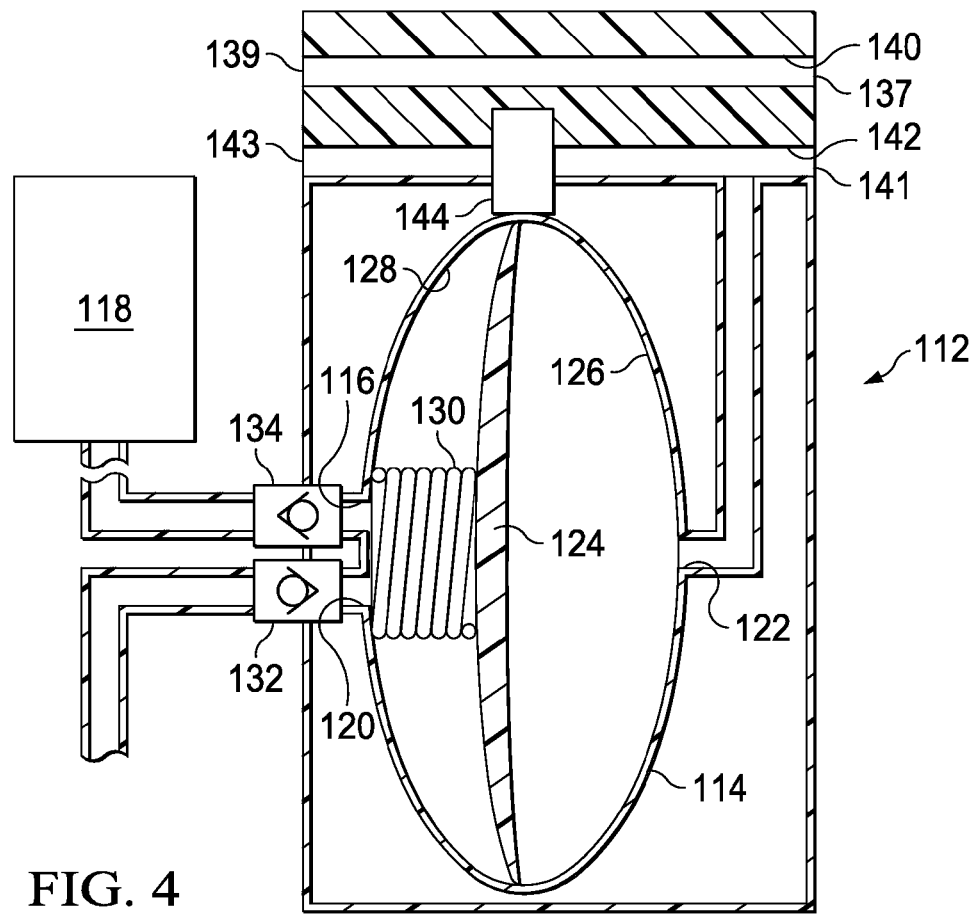
FIG. 4 is a schematic sectional diagram illustrating additional details that may be associated with operations of an example embodiment of the cartridge of FIG. 2.

Some operations of the therapy system 100 may be described with respect to FIG. 2, FIG. 3, and FIG. 4, which is a schematic sectional diagram illustrating additional details that may be associated with some example operations of the cartridge 112 in a second state. Generally, the first end 141 of the therapy conduit 142 may be fluidly coupled to the therapy port 162. The fluid coupling may place the therapy conduit 142 in fluid communication with the vent valve 156, the pump pressure sensor 154, and the selector valve 148. Similarly, the first end 137 of the pressure-sensing conduit 140 may be fluidly coupled to the pressure-sensing port 164. The fluid coupling may place the pressure-sensing conduit 140 in fluid communication with the pressure-relief valve 160 and the therapy-pressure sensor 158. The canister 113 may be fluidly coupled to the second end 143 of the therapy conduit 142 and the second end 164 of the pressure-sensing conduit 140.

In some embodiments, the therapy system 100 may be operated in a negative-pressure therapy mode. In the negative-pressure therapy mode, the controller 152 may position the selector valve 148 in the first position so that the pump inlet 145 is in fluid communication with the pump pressure sensor 154 and the vent valve 156. In the first position, the pump outlet 147 is in fluid communication with the vent 150. The controller 152 may operate the pump 146 to draw fluid through the therapy port 162 and the pump inlet 145, and move fluid out of the pump outlet 147 and the vent 150. Fluid may also be drawn from the canister 113 through the therapy conduit 142. The valve 144 may be opened to permit fluid flow from the second end 143 of the therapy conduit 142 to the first end 141 of the therapy conduit 142. In this manner, the pump 146 may generate a negative pressure in the canister 113 that may be communicated to the dressing 102. The pump pressure sensor 154 and the therapy-pressure sensor 158 may determine the pressure in the therapy conduit 142 and the pressure-sensing conduit 140, respectively, and communicate the pressures to the controller 152. In response, the controller 152 may adjust the operation of the therapy system 100 to provide a predetermined negative-pressure therapy.

In some embodiments, fluid may also be drawn through the pressure inlet 122 through the fluid coupling of the pressure inlet 122 with the therapy conduit 142. The fluid movement may also generate a negative pressure in the pressure chamber 126. The negative pressure generated in the pressure chamber 126 may cause a pressure differential across the diaphragm 124, urging the diaphragm 124 toward the pressure inlet 122 and the charge position, as shown in FIG. 2. In some embodiments, fluid may flow from the fluid source 118 into the dosing chamber 128 in response to the movement of the diaphragm 124 to the charge position.

At the conclusion of negative-pressure therapy, the controller 152 may operate the vent valve 156 and the pressure-relief valve 160 to equalize the pressure in the canister 113 and the dressing 102 to the ambient pressure. For example, the pressure-relief valve 160 may be opened to permit fluid to flow from the ambient environment into the canister 113 and the dressing 102, decreasing the negative-pressure in the canister 113 and the dressing 102. Similarly, the vent valve 156 may be opened to permit fluid to flow from the ambient environment into the cartridge 112, decreasing the negative-pressure in the pressure chamber 126.

In some embodiments, the pressure-relief valve 160 may be used to clear blockages in the pressure sensing conduit 140. In some embodiments, vent valve 156 may be used by the controller 152 to determine if the canister 113 is full. In some embodiments, the controller 152 may vent the canister 113 through the vent valve 156 and measure a rate of change of negative pressure. If the negative pressure in the canister 113 changes below a predetermined threshold rate of change of negative pressure, then the canister 113 may be empty. If the negative pressure in the canister 113 changes above a predetermined threshold rate of change of negative pressure, then the canister 113 may be full.

In some embodiments, the therapy system 100 may be operated in an instillation therapy mode. In the instillation therapy mode, the controller 152 may position the selector valve 148 in the second position so that the pump inlet 145 is in fluid communication with the vent 150. In the second position, the pump outlet 147 is in fluid communication with the pump therapy port 162. The controller 152 may operate the pump 146 to draw fluid through the vent 150 and move fluid out of the therapy port 162. Fluid may be moved into the therapy conduit 142. The valve 144 may be closed to prevent fluid flow from the first end 141 of the therapy conduit 142 to the second end 143 of the therapy conduit 142. In this manner, the pump 146 may generate a positive pressure in the therapy conduit 142 that may be communicated to the pressure inlet 122. The pump pressure sensor 154 and the therapy-pressure sensor 158 may determine the pressure in the therapy conduit 142 and the pressure-sensing conduit 140, respectively, and communicate the pressures to the controller 152. In response, the controller 152 may adjust operation of the therapy system 100 to provide a predetermined instillation therapy.

As shown in FIG. 4, the fluid movement into the pressure inlet 122 may generate a positive pressure in the pressure chamber 126. The positive pressure may cause a pressure differential across the diaphragm 124, urging the diaphragm 124 toward the fluid inlet 116, the fluid outlet 120, and the discharge position. In some embodiments, the valve 134 may be closed, and the valve 132 may be opened, allowing fluid to flow from the dosing chamber 128 through the fluid outlet 120. Generally, the positive pressure generated by the pressure source 104 may apply a force to the diaphragm 124 that moves the diaphragm 124 to the fluid inlet 116, compressing the dosing chamber 128. In response, the spring 130 may be loaded and exert a reactive force on the diaphragm 124. Generally, the positive pressure generated in the pressure chamber 126 may overcome the reactive force of the spring 130, compressing the spring 130 as shown in FIG. 4.

If the diaphragm 124 reaches the discharge position illustrated in FIG. 4, the controller 152 may stop the operation of the pump 146. For example, the controller 152 may determine that the pressure calculated by the pump pressure sensor 154 may be stable, that is neither increasing nor decreasing beyond a predetermined range. In response, the controller 152 may open the vent valve 156 to the ambient environment, allowing the pressure in the pressure chamber 126 to equalize with the pressure in the ambient environment. In response, the reactive force generated by the compression of the spring 130 may act on the diaphragm 124, urging the diaphragm 124 toward the pressure inlet 122 as the pressure in the pressure chamber 126 approaches the ambient pressure. The movement of the diaphragm 124 toward the pressure inlet 122 may expand the dosing chamber 128, generating a negative pressure in the dosing chamber 128. The valve 132 may be closed, and the valve 134 may be opened, so that the negative pressure in the dosing chamber 128 may draw fluid from the fluid source 118 through the fluid inlet 116 and into the dosing chamber 128, refilling the dosing chamber 128. If the diaphragm 124 reaches the charge position of FIG. 2, the controller 152 may close the vent valve 156. For example, the controller 152 may determine that the pressure calculated by the pump pressure sensor 154 may be stable, that is neither increasing nor decreasing beyond a predetermined range. The controller 152 may operate the pump 146 to again move fluid into the pressure chamber 126 and provide another instillation dose to the dressing 102.

In some embodiments, the dosing chamber 128 may be sized to hold a predetermined dose of instillation fluid for instillation of a tissue site. For example, if the diaphragm 124 is in the charge position illustrated in FIG. 2, the dosing chamber 128 may have a volume substantially equal to the amount of fluid necessary to provide a therapeutic dose of instillation fluid to a tissue site. A therapeutic dose of instillation fluid may be a volume of fluid required to be delivered to a tissue site to provide suitable therapeutic benefits to the tissue site. In other embodiments, the volume of the dosing chamber 128 may be larger or smaller than the therapeutic dose of instillation fluid.

In some embodiments, the cartridge 112 may not include the spring 130. In some embodiments without the spring 130, movement of the diaphragm 124 may be accomplished by operating the selector valve 148 to switch from drawing fluid to generate a negative pressure that moves the diaphragm 124 to the charge position. If the diaphragm 124 reaches the charge position, the selector valve 148 may be operated to move fluid into the pressure chamber 126, generating a positive pressure in the pressure chamber 126 and moving the diaphragm 124 to the discharge position to provide the instillation dose.

FIG. 5 is a schematic diagram, illustrating additional details of a coupling system for the therapy system 100. In some embodiments, the pressure source 104, the cartridge 112, and the canister 113 may be coupled directly to one another so that the pressure source 104, the cartridge 112, and the canister 113 may be manipulated as a single body. In some embodiments, the direct coupling may be accomplished by way of a latching system. For example, the pressure source 104 may include a tang 200 extending from the pressure source 104. The tang 200 may have a generally wedge shape having a narrower end distal from the pressure source 104 and a broader end proximate to the pressure sourced 104. In some embodiments, the tang 200 may include a notch 202 proximate to the distal end. The notch 202 may be disposed across a surface of the tang 200. In some embodiments, the tang 200 may increase in cross-sectional width from the notch 202 to the proximate end of the tang 200.

In some embodiments, the cartridge 112 may include release lever 204. The release lever 204 may include a notch 205 that may be positioned on the release lever 204 to mate with the notch 202. In some embodiments, the release lever 204 may include a handle 207 extending from the notch 205. The handle 207 may extend from the notch 205 outwardly from the cartridge 112. In some embodiments, the cartridge 112 may also include a tang 206 extending from the cartridge 112. The tang 206 may have a generally wedge shape having a narrower end distal from the cartridge 112 and a broader end proximate to the cartridge 112. In some embodiments, the tang 206 may include a notch 208 proximate to the distal end. The notch 208 may be disposed across a surface of the tang 206. In some embodiments, the tang 206 may increase in cross-sectional width from the notch 208 to the proximate end of the tang 206.

In some embodiments, the canister 113 may include release lever 210. The release lever 210 may include a notch 209 that may be positioned on the release lever 210 to mate with the notch 208. In some embodiments, the release lever 210 may include a handle 212 extending from the notch 209. The handle 212 may extend from the notch 209 outwardly from the canister 113.

In some embodiments, the cartridge 112 may be coupled to the pressure source 104 by placing the cartridge 112 proximate to the pressure source 104 so that the notch 202 and the notch 205 may engage each other. In some embodiments, the notch 202 and the notch 205 may have facing surfaces that contact one another to prevent the cartridge 112 from slipping relative to the pressure source 104. To release the cartridge 112 from the pressure source 104, the handle 207 may be moved away from the tang 200, disengaging the notch 205 from the notch 202. In a similar manner, the canister 113 may be coupled to and released from the cartridge 112. In some embodiments, the cartridge 112 may not be used and the canister 113 may be coupled directly to the pressure source 104.

In other embodiments, a pressure source may use other mechanisms to secure a canister to the pressure source. A cartridge may be configured to engage both the male and female components of other mechanisms so that the cartridge may be coupled to a wide range of pressure sources. For example, an ActiVAC system produced by Kinetic Concepts, Inc. may have a proprietary latching mechanism to secure a canister to a pressure source. A cartridge could be manufactured to engage the proprietary system so that the cartridge may be directly coupled to both the pressure source and the canister as generally described above.

Example embodiments of the cartridge have been described herein that can be combined with a negative-pressure wound treatment therapy system to provide controlled instillation therapy. The cartridge can also be calibrated to provide a dosage of fluid at a pressure suitable for use with a tissue site, for example, approximately 100 mmHg. The cartridge can also be calibrated to provide an accurate dosing of a prescribed amount of fluids, for example a 5 milliliter dosage of fluid. The therapy system described herein may also be used to provide both negative-pressure therapy and instillation therapy. The therapy system also provides a disposable cartridge for the provision of instillation therapy with a single pressure source without requiring changeover of equipment to switch between negative-pressure therapy and instillation therapy.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for providing instillation therapy and negative-pressure therapy with a pressure source, the apparatus comprising:

a therapy conduit configured to be fluidly coupled on a first end to the pressure source, fluidly coupled on a second end to a canister, and further configured to be fluidly coupled to a dressing;

a housing having a fluid inlet configured to be fluidly coupled to a fluid source, a fluid outlet configured to be fluidly coupled to the dressing, and a pressure inlet fluidly coupled to the therapy conduit;

a moveable barrier disposed in the housing to form a dosing chamber and a pressure chamber, the dosing chamber and the pressure chamber fluidly isolated from each other, the fluid inlet and the fluid outlet in fluid communication with the dosing chamber, and the pressure inlet in fluid communication with the pressure chamber;

a biasing element disposed in the dosing chamber, coupled to the moveable barrier, and operable to move the moveable barrier between a discharge position and a charge position; and a check valve fluidly coupled to the therapy conduit and the pressure inlet.

2. The apparatus of claim 1, wherein the check valve is a reed valve.

3. The apparatus of claim 1, wherein the housing is configured to be coupled between the pressure source and the canister.

4. The apparatus of claim 1, further comprising a pressure-sensing conduit configured to be fluidly coupled to the canister and a pressure sensor.

5. The apparatus of claim 1, wherein the moveable barrier comprises a diaphragm.

6. The apparatus of claim 1, wherein the moveable barrier comprises a piston.

7. The apparatus of claim 1, wherein the biasing element comprises a spring.

8. The apparatus of claim 1, wherein:
the biasing element comprises a spring;
the spring is in a loaded position when the moveable barrier is in the discharge position; and
the spring is in an unloaded position when the moveable barrier is in the charge position.

9. The apparatus of claim 1, wherein:
the biasing element comprises a spring;
the spring is in a loaded position when the moveable barrier is in the charge position; and
the spring is in an unloaded position when the moveable barrier is in the discharge position.

10. The apparatus of claim 1, further comprising a fluid inlet valve fluidly coupled to the fluid inlet.

11. The apparatus of claim 1, further comprising a fluid outlet valve fluidly coupled to the fluid outlet.

12. The apparatus of claim 1, further comprising:
a fluid inlet valve fluidly coupled to the fluid inlet; and
a fluid outlet valve fluidly coupled to the fluid outlet.

13. The apparatus of claim 10, wherein the fluid inlet valve is a check valve permitting fluid flow into the dosing chamber.

14. The apparatus of claim 11, wherein the fluid outlet valve is a check valve permitting fluid flow out of the dosing chamber.

15. The apparatus of claim 12, wherein:
the fluid inlet valve is a check valve permitting fluid flow into the dosing chamber; and
the fluid outlet valve is a check valve permitting fluid flow out of the dosing chamber.

16. A therapy system for providing instillation therapy and negative-pressure therapy, the system comprising:

a pump having a pump inlet and a pump outlet, the pump configured to draw fluid into the pump inlet and move fluid out of the pump outlet;

a fluid source;

an adapter coupled to the pump and the fluid source, the adapter comprising:
a therapy conduit configured to be fluidly coupled on a first end to the pump and on a second end to a canister;

a housing having a fluid inlet configured to be fluidly coupled to the fluid source, a fluid outlet configured to be fluidly coupled to a dressing, and a pressure inlet fluidly coupled to the therapy conduit;

a moveable barrier disposed in the housing to form a dosing chamber and a pressure chamber, the dosing chamber and the pressure chamber fluidly isolated from each other, the fluid inlet and the fluid outlet in fluid communication with the dosing chamber, and the pressure inlet in fluid communication with the pressure chamber;

a biasing element disposed in the dosing chamber, coupled to the moveable barrier, and operable to move the moveable barrier between a discharge position and a charge position; and a check valve fluidly coupled to the therapy conduit and the pressure inlet; and a selector valve fluidly coupled to the pump inlet and the pump outlet and configured to be fluidly coupled to the therapy conduit, the selector valve having a first position fluidly coupling the pump inlet to the therapy conduit and a second position fluidly coupling the pump outlet to the therapy conduit.

17. The system of claim 16, wherein the selector valve comprises a four way valve.

18. The system of claim 16, wherein the check valve is a reed valve.

19. The system of claim 16, wherein the system is configured to be coupled between the pump and the canister.

20. The system of claim 16, further comprising a pressure-sensing conduit configured to be fluidly coupled to the canister and a pressure sensor.

21. The system of claim 16, wherein the moveable barrier comprises a diaphragm.

22. The system of claim 16, wherein the moveable barrier comprises a piston.

23. The system of claim 16, wherein the biasing element comprises a spring.

24. The system of claim 16, wherein:
the biasing element comprises a spring;
the spring is in a loaded position when the moveable barrier is in the discharge position; and
the spring is in an unloaded position when the moveable barrier is in the charge position.

25. The system of claim 16, wherein:
the biasing element comprises a spring;
the spring is in a loaded position when the moveable barrier is in the charge position; and
the spring is in an unloaded position when the moveable barrier is in the discharge position.

26. The system of claim 16, further comprising a fluid inlet valve fluidly coupled to the fluid inlet.

27. The system of claim 16, further comprising a fluid outlet valve fluidly coupled to the fluid outlet.

28. The system of claim 16, further comprising:
a fluid inlet valve fluidly coupled to the fluid inlet; and
a fluid outlet valve fluidly coupled to the fluid outlet.

29. The system of claim 26, wherein the fluid inlet valve is a check valve permitting fluid flow into the dosing chamber.

30. The system of claim 27, wherein the fluid outlet valve is a check valve permitting fluid flow out of the dosing chamber.

31. The system of claim 28, wherein:
the fluid inlet valve is a check valve permitting fluid flow into the dosing chamber; and
the fluid outlet valve is a check valve permitting fluid flow out of the dosing chamber.

32. A method for providing instillation therapy and negative-pressure therapy, the method comprising:
providing a pressure source having a selector valve;
providing a canister;
providing a fluid source;
providing a dressing;
providing an adapter comprising:
a therapy conduit;
a housing having a fluid inlet, a fluid outlet, and a pressure inlet fluidly coupled to the therapy conduit;
a moveable barrier disposed in the housing to form a dosing chamber and a pressure chamber, the dosing chamber and the pressure chamber fluidly isolated from each other, the fluid inlet and the fluid outlet in fluid communication with the dosing chamber, and the pressure inlet in fluid communication with the pressure chamber;
a biasing element disposed in the dosing chamber, coupled to the moveable barrier, and operable to move the moveable barrier between a discharge position and a charge position; and
a check valve fluidly coupled to the therapy conduit and the pressure inlet;
fluidly coupling the therapy conduit to the pressure source and the canister;
fluidly coupling the fluid source to the fluid inlet;
fluidly coupling the fluid outlet to the dressing;
operating the selector valve to select a therapy mode; and
operating the pressure source in response to the therapy mode selection.

33. The method of claim 32, wherein operating the selector valve to select a therapy mode comprises:
if a negative-pressure therapy mode is selected, fluidly coupling a pump inlet of the pressure source to the therapy conduit and a pump outlet to a vent of the pressure source; and
if an instillation therapy mode is selected, fluidly coupling the pump inlet of the pressure source to the vent of the pressure source and the pump outlet of the pressure source to the therapy conduit.

34. The method of claim 32, wherein the therapy mode is a negative-pressure therapy mode and the method further comprises:
operating the pressure source to draw fluid through the therapy conduit and the canister to generate a negative pressure.

35. The method of claim 32, wherein the therapy mode is an instillation therapy mode and the method further comprises:
operating the pressure source to move fluid into the pressure chamber through the therapy conduit and the pressure inlet, generating a positive pressure in the pressure chamber; and
in response to the positive pressure, moving the moveable barrier to the discharge position to move fluid from the dosing chamber through the fluid outlet.

36. The method of claim 32, wherein the selector valve comprises a four way valve.

37. The method of claim 32, wherein the check valve is a reed valve.

38. The method of claim 32, further comprising fluidly coupling a pressure-sensing conduit to the pressure source and the canister.

39. The method of claim 32, wherein the moveable barrier comprises a diaphragm.

40. The method of claim 32, wherein the moveable barrier comprises a piston.

41. The method of claim 32, wherein the method further comprises actuating the biasing element to move the moveable barrier to a charge position, drawing fluid from the fluid source into the dosing chamber.

42. The method of claim 32, wherein the biasing element comprises a spring.

43. The method of claim 32, wherein:
the biasing element comprises a spring;
the spring is in a loaded position when the moveable barrier is in the discharge position; and
the spring is in an unloaded position when the moveable barrier is in the charge position.

44. The method of claim 32, wherein:
the biasing element comprises a spring;
the spring is in a loaded position when the moveable barrier is in the charge position; and
the spring is in an unloaded position when the moveable barrier is in the discharge position.

45. The method of claim 32, further comprising a fluid inlet valve fluidly coupled to the fluid inlet.

46. The method of claim 32, further comprising a fluid outlet valve fluidly coupled to the fluid outlet.

47. The method of claim 32, further comprising:
a fluid inlet valve fluidly coupled to the fluid inlet; and
a fluid outlet valve fluidly coupled to the fluid outlet.

48. The method of claim 45, wherein the fluid inlet valve is a check valve permitting fluid flow into the dosing chamber.

49. The method of claim 46, wherein the fluid outlet valve is a check valve permitting fluid flow out of the dosing chamber.

50. The method of claim 47, wherein:
the fluid inlet valve is a check valve permitting fluid flow into the dosing chamber; and
the fluid outlet valve is a check valve permitting fluid flow out of the dosing chamber.

51. An apparatus for providing installation therapy and negative-pressure therapy, the apparatus comprising:
a housing;
a moveable barrier disposed in the housing to form a dosing chamber and a pressure chamber;
a therapy conduit configured to be fluidly coupled to a pressure source and to a canister;
a fluid inlet fluidly coupled to the dosing chamber and configured to be fluidly coupled to a fluid source;
a fluid outlet fluidly coupled to the dosing chamber and configured to be fluidly coupled to a dressing;
a pressure inlet fluidly coupled to the therapy conduit and the pressure chamber;
a biasing element disposed in the dosing chamber, coupled to the moveable barrier, and operable to move the moveable barrier between a discharge position and a charge position; and
a check valve in the therapy conduit.

52. The apparatus of claim 51, wherein the check valve is a reed valve.

53. The apparatus of claim 51, wherein the moveable barrier comprises a diaphragm.

54. The apparatus of claim 51, wherein the moveable barrier comprises a piston.

55. The apparatus of claim 51, wherein:
the biasing element comprises a spring;
the spring is in a loaded position when the moveable barrier is in the discharge position; and
the spring is in an unloaded position when the moveable barrier is in the charge position.

56. The apparatus of claim 51, wherein:
the biasing element comprises a spring;
the spring is in a loaded position when the moveable barrier is in the charge position; and
the spring is in an unloaded position when the moveable barrier is in the discharge position.

57. The apparatus of claim 51, further comprising:
a fluid inlet valve fluidly coupled to the fluid inlet; and
a fluid outlet valve fluidly coupled to the fluid outlet.

58. The apparatus of claim 57, wherein:
the fluid inlet valve is a check valve permitting fluid flow into the dosing chamber; and
the fluid outlet valve is a check valve permitting fluid flow out of the dosing chamber.

59. The apparatus of claim 51, wherein the check valve is fluidly coupled between the pressure inlet and the canister.

* * * * *